United States Patent [19]

Kopke

[11] Patent Number: 4,748,598
[45] Date of Patent: May 31, 1988

[54] METHOD TO CALIBRATE ACOUSTIC INSTRUMENTS, AND CALIBRATION SYSTEM

[75] Inventor: Wolfgang Kopke, Berlin, Fed. Rep. of Germany

[73] Assignee: Robert Bosch GmbH, Stuttgart, Fed. Rep. of Germany

[21] Appl. No.: 876,821

[22] Filed: Jun. 20, 1986

[30] Foreign Application Priority Data

Aug. 20, 1985 [DE] Fed. Rep. of Germany ....... 3529704

[51] Int. Cl.$^4$ ............................................. H04B 17/00
[52] U.S. Cl. .................................... 367/13; 73/1 DV; 73/585
[58] Field of Search ............... 367/13; 73/1 R, 1 DV, 73/585

[56] References Cited

U.S. PATENT DOCUMENTS

| | | | |
|---|---|---|---|
| 3,942,150 | 3/1976 | Booth et al. ........................... | 367/13 |
| 3,959,770 | 5/1976 | Schaefer ................................ | 367/13 |
| 4,240,281 | 12/1980 | Lather et al. ...................... | 73/1 DV |
| 4,615,007 | 9/1986 | King et al. ............................ | 73/585 |

OTHER PUBLICATIONS

Short, Microprocessors and Programmed Logic, 1981, pp. 38–39.
Fiedler/Wassenberg "Handbuch der Medizintechnik" pp. 5–7.
"Handbook of Clinical Audiology" 1978, pp. 179–187.

Primary Examiner—Thomas H. Tarcza
Assistant Examiner—Daniel T. Pihulic
Attorney, Agent, or Firm—Frishauf, Holtz, Goodman & Woodward

[57] ABSTRACT

To provide for permanent calibration of an audiometer, for example, to hold the calibration even in case of an interruption of supply voltage, an electrically erasable programmable and reprogrammable read-only memory (EEPROM) (15) receives calibration data in a closed loop by comparing the output of a transducer (13) with the input to a measuring microphone (31), in digital form and after digitizing, with command outputs stored in a computer (22). A tone generator (11), likewise controlled by the computer, provides control frequencies via a controlled amplifier (12) to the transducer (13). The calibrating EEPROM (15) receives correction data from the computer via a data bus (29) which, in turn, controls the resistance of a switchable resistance (18, 181) to provide a correction voltage to the amplifier (12).

12 Claims, 2 Drawing Sheets

METHOD TO CALIBRATE ACOUSTIC INSTRUMENTS, AND CALIBRATION SYSTEM

The present invention relates to electroacoustic measuring apparatus, and more particularly to audiometers, to test frequency and amplitude response of the hearing of persons to be tested, and especially to methods and systems to easily permit calibration of audiometers and similar apparatus.

BACKGROUND

Manual calibration of audiometers is well known—see the referenced article in "Handbook of Medical Technology", by Fiedler/Wassenberg, 2nd Supplement, February 1984, II-2.1.11 attachment, pages 5–7. Such calibration is time-consuming and costly. Electroacoustic measuring apparatus can also be calibrated automatically, but such automatic calibration systems have the disadvantage that calibration values which are derived are appropriate only for the then existing test; upon disconnection, the audiometer, after termination of a test, or due to loss of operating voltage for whatever reason—failure of a battery or the like for example—the audiometer must be recalibrated.

THE INVENTION

It is an object to provide a calibration method and system in which the audiometer, once calibrated, will retain the calibration; if desired, recalibration can be easily effected, so that the appropriate calibration will always be the one which is employed for tests.

Briefly, calibration values are stored in an electrically programmable read-only memory, for example an electrically erasable programmable read-only memory (EEPROM), which receives digital correction data. The digital correction data are read during measuring use of the test apparatus, and correction values are applied to the measured values.

In accordance with a preferred feature of the invention, the measuring instrument is coupled to an electronic computer which operates digitally; the electronic computer, in its memory, stores desired or command values. The actually measured values, after conversion into digital values, are compared with the desired or command values and, from such comparison, an error or deviation calibration value is obtained, if there should be deviation in the actual measured value. The calibration values then are entered into the electronic memory, for example the EEPROM. Thus, the data stored in the EEPROM can be updated at any time by erasing previously entered data or updating data by new ones. The electronic memory, thus, will always have the appropriate and latest calibration values entered therein. Deviations between actual and desired values may, for example, arise due to aging of components or interchange of apparatus or devices used in the audiometer, for example a microphone, and circuitry in connection with amplification of sound at specific frequencies.

DRAWINGS

FIG. 1 is a schematic block circuit diagram of an audiometer in which all elements not necessary for an understanding of the present invention have beem omitted, and showing, specifically, the calibration system, carrying out the method; and FIG. 2 is a block circuit diagram of a calibrating memory, a calibrating switching apparatus and a calibrating resistance divider chain.

DETAILED DESCRIPTION

Figure 1:
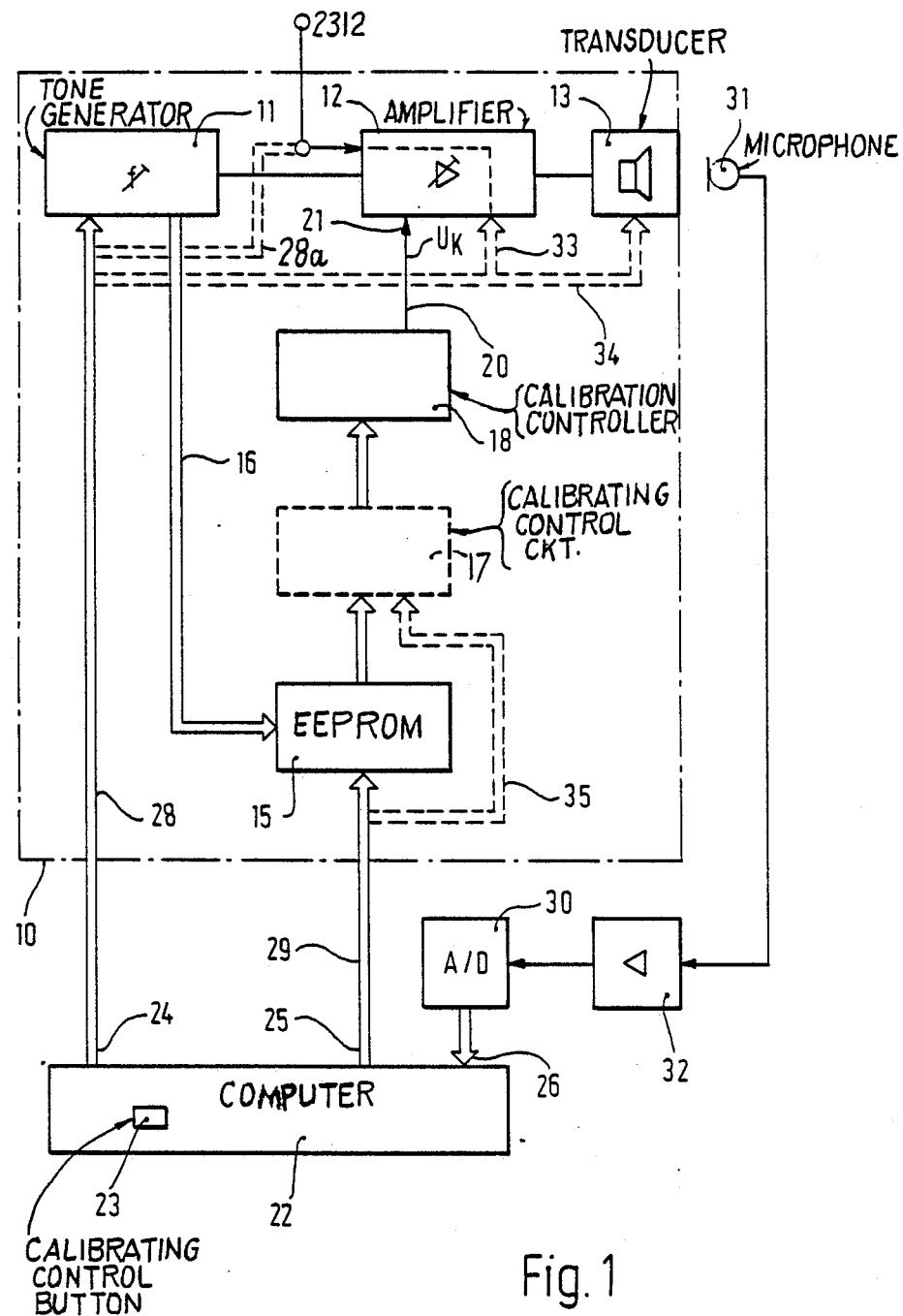

The chain-dotted line in FIG. 1 schematically represents the network portion of an audiometer 10. The audiometer, as is customary, includes a tone or acoustic frequency generator 11, which is coupled to an amplifier 12 of variable and controllable amplification. Amplifier 12 is coupled to a transducer 13, for example earphones, a loudspeaker, or the like. Sound from the transducer 13 is also picked up by a pick-up microphone or similar apparatus 31 as will appear. In a preferred form, the transducer 13 is a loudspeaker.

The frequency of the generator 11 and the amplification of the amplifier 13 can be controlled and set in steps.

Elements 11, 12, 13 can be of any suitable and standard construction and part of a standard audiometer. On and beyond these known components, the audiometer includes a non-volatile, that is, read-only electrically erasable and reprogrammable read-only memory 15. Memory 15 is, preferably, an EEPROM unit. EEPROM 15 can be addressed and accessed from the tone generator via an address bus 16. The EEPROM is connected to a calibrating control circuit 17 which, in turn, is connected to a calibration controller 18. Calibration controller 18, preferably—and as will be described in detail with respect to FIG. 2—is a calibration resistance divider chain. The output of the calibration controller 18 is connected over a control line 20 with an amplification control input 21 of the amplifier 12.

The audiometer so far described is connected to and has associated therewith an electronic computer or controller 22. Computer 22 has a separate control command button 23. Control command button 23 places the computer in the calibration mode. The computer has a first output 24 which is coupled via an address bus 28 to the tone generator 11 to control the frequency thereof; computer 22 has a second output 25 which is connected over a data and programming bus 29 to the erasable electrically programmable read-only memory (EEPROM) 15. Computer 22 has an input 26 which is coupled to the output of an analog/digital (A/D) converter 30. A measuring microphone, that is, an acoustic-to-electrical transducer 31, is acoustically coupled to the transducer 13. Its output is amplified in an amplifier 32 which, in turn, is connected to the input of the A/D converter 30.

OPERATION

Let it be assumed that operating voltage is available. For calibration, the calibrating control button 23 of the computer 22 is operated. The computer 22 is programmed to store a calibration program. In accordance with the calibration program, the computer 22 will control, via the bus 28, the tone generator to emit a tone at a first frequency $f_1$. The tone frequency signal is amplified in the amplifier 12. The amplifier 12, upon receiving the first tone frequency $f_1$, will provide an amplification factor which can be set manually be setting a first amplification factor at a control input 2312. Alternatively, the amplification of the amplifier can be controlled in steps from the computer 22 to provide an initial amplification factor during calibration. Since either possibility can be used, bus 28 is shown to have a branch line 28a to provide for automatic control of the amplification factor of the amplifier 12, upon calibration, which can be over-ridden by a manual amplification control set button or knob 2312.

Tone generator 11, further, provides over address bus 16 an addressing signal in form of a data word to the EEPROM 15, in which the addressing signal corresponds to that of the initial tone frequency $f_1$. The EEPROM provides a data word corresponding to the address stored in the EEPROM and corresponding to the frequency $f_1$; the data word so switches the calibration controller 18 that its output will provide a predetermined calibration voltage $U_K$. This voltage may provide a correction of the calibration level set either by hand from knob 2312 or automatically upon operation of the calibrating control button 23 of the computer. The initial setting of the amplifier 12, thus, can be carried out manually by control of the knob 2312 or automatically from the branch bus 28a branching from bus 28, in which case the automatic calibration can be over-riden by the manual control knob 2312, to provide the initial amplification setting for the amplifier 12.

The tone signal at frequency $f_1$ from the tone generator 11 is being amplified in the amplifier 12 at a predetermined initial amplification level, and applied to the transducer 13. The tone emitted from the transducer 13 is received in the microphone or transducer 31, providing a sensed outut voltage which is amplified in the amplifier 32, and converted into a digital word in the A/D converter 30. The digital data word received at the input 26 of the computer is compared in the computer with the level that it should have.

Two possibilities present themselves:

(1) No deviation is determined in the computer between actual measured value at input 26 and command value stored in the computer for the frequency $f_1$. The computer then switches, via address bus 28, the tone generator 11 to the next tone frequency, for example $f_2$. Calibration with respect to the frequency $f_2$ will then proceed similarly to the calibration previously described in connection with tone frequency $f_1$. Again, a certain amplification is set into the amplifier 12, either again manually or automatically via bus 28 and branch bus 28a.

(2) Computer 22 determines that there is a difference between the actual measured value at input 26 and the command value as set in the computer. A data word corresponding to the difference or deviation is generated and provided at output 25 to the data and programming bus 29, for recording in the EEPROM 15. If the EEPROM should, already, have a deviation word stored therein, the deviation word is modified or upgraded or updated in accordance with the then generated output from the computer 22. The calibration control circuit 17—if used—and the calibration controller 18 then will apply a new calibration voltage value $U_K$ to the control input 21 of the amplifier 12.

The course of the calibration and the run thereof is controlled by the computer 22. This calibration step is repeated once more, that is, as soon as the amplifier 13 has reached its new level, the microphone 31, via amplifier 32 and A/D converter 26, will provide its output to input 26 of the computer, for comparison, in digital form, with the command or desired value for the frequency $f_1$ in the computer. If there continues to be a difference, a subsequent control of amplification is effected. Only when there is no difference between command value and actual value, will the tone generator 11 switch to the next frequency $f_2$.

Figure 2:
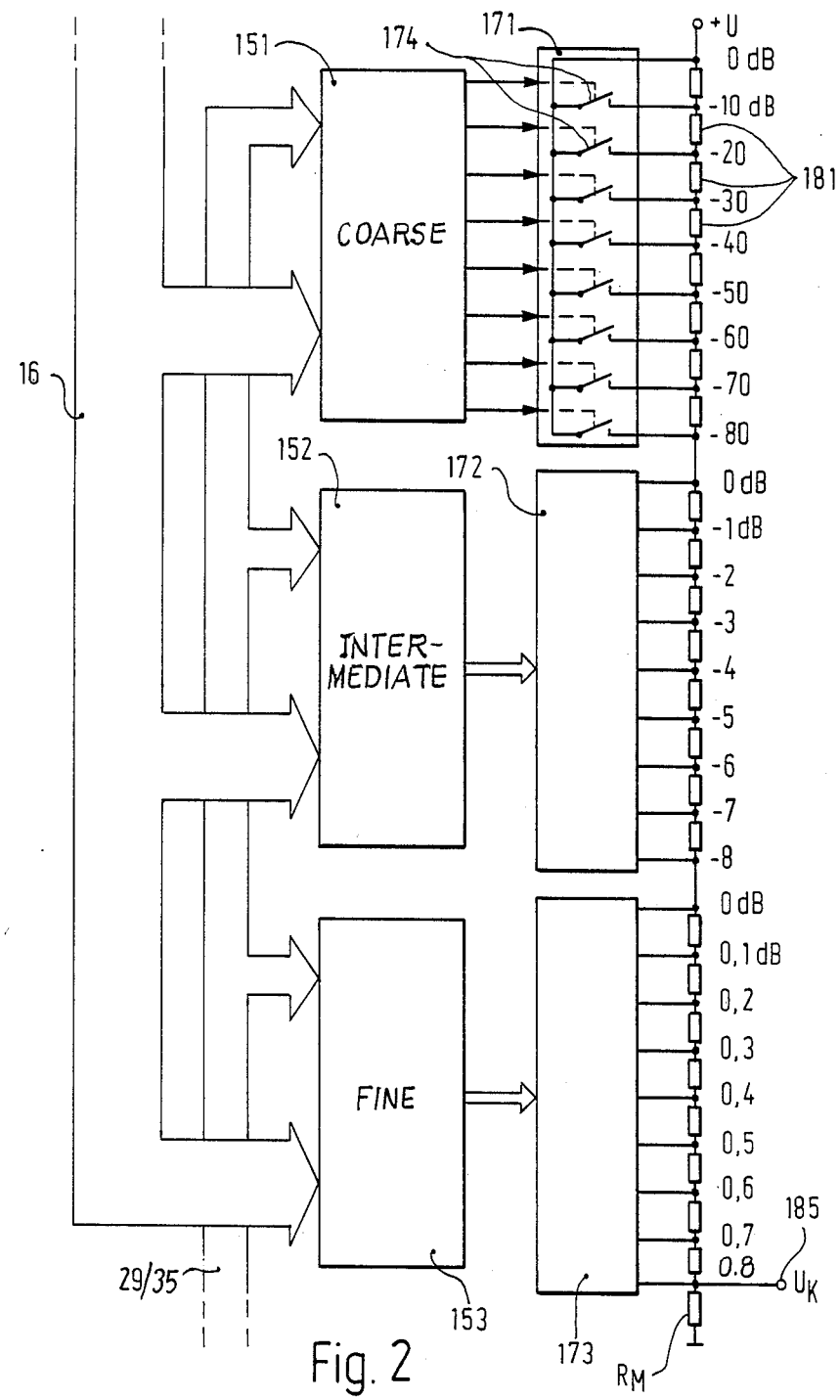

A suitable circuit for coarse, intermediate and fine calibration, which are different degrees of fineness, or resolution of calibration, is shown in FIG. 2. The EEPROM 15—see FIG. 1—is so made that it provides three memory sets or groups for, respectively, coarse, intermediate and fine calibration, that is, three submemories 151, 152, 153. The calibrating submemories are addressed, in parallel, via a data word, corresponding to the particular tone frequency—e.g. $f_1$—of the tone generator 11 from the address bus, see FIG. 1. The digital information, stored in the memory cells of the EEPROM 15 or, rather, in the submemories 151, 152, 153, control switching circuits 171, 172, 173, forming part of a calibration control circuit 17. The calibration control circuit 17, via the switching arrangements 171, 172, 173, control the connection of respective resistors 181 of a resistance chain forming the calibration controller 18. Each one of the switch groups 171, 172, 173 has eight switches 174 which, when closed, short-circuit the respective resistors 181, as seen in FIG. 2. The resistance chain 181 is connected between a voltage, preferably a controlled voltage $+U$, and ground or chassis. The calibration voltage $U_K$ is connected between a terminal 185 and ground or chassis, that is, is picked off a measuring resistor $R_M$, preferably a precision resistor. In dependence on the resistances 181 which have not been short-circuited by respective switches 174, a predetermined calibration voltage $U_K$ will appear at the terminal 185. The resistance values are so selected that steps, shown next to the resistors in FIG. 2, of 0 ... 80 dB; 0 ... 8 dB and 0 ... 0.8 dB will result.

The basic system has been described in connection with FIGS. 1 and 2; various changes and modifications may be made, and not all features as described are strictly necessary. For example, an address bus 34 can be coupled to the bus 28 from the computer to provide for output commands to a different type of transducer. For example, transducer 13 may be an acoustically tone emitting loudspeaker; rather than using a loudspeaker, a bone conduction transducer could be used which then, may require a different calibration. Upon suitable control of the computer, different calibration outputs, in dependence on the selected transducer, can be connected or controlled or commanded to provide the respective output. Alternatively, rather than using a bone conduction transducer, an air or ear-canal transfer ear-phone can be connected; characteristics which will differ from those of a loudspeaker can be stored in the memory of the computer. Suitable commands of the amplifier 12 are entered into the amplifier by a branch bus 33.

The bus 28 can control the tone generator to provide tone signals of different wave form; normally, the tone generator will provide frequencies which are sinusoidal; rather than using sinusoidal signals of a predetermined frequency, random noise signals within frequency ranges can be generated, and calibration carried out, as described in connection with a predetermined frequency with such noise signals.

The computer 22 can, additionally, be programmed to provide data via the address bus 28 to the tone generator 11 to generate an amplitude modulated outut frequency, used for example in the SISI test. This test is described in Jack Katz, "Handbook of Clinical Audiology", 1978, pages 179 to 187.

The setting of the amplifier 12, upon calibration, can be accelerated during the calibration step by initially bypassing the memory 15, as shown in broken lines by bus 35. Thus, the data and programming bus 29 will be directly connected to the calibration control circuit 17. The data words generated when command value and actual value are identical—as determined by the computer 22—are then entered into the EEPROM 15. Only when the calibration is compled will the memory 15 record the new value, which somewhat accelerates the recording and calibration operation but requiring more complex software.

The calibration control circuit 17, while highly desirable and shown as a group of switches 174, coupled in groups 171, 172, 173 to the memory 15, is not as such strictly necessary, and the calibration switching can be combined with the controller 18. Calibration control circuit 17, thus, is shown in broken lines in FIG. 1 since its function can be integrated in the controller 18.

Various changes and modifications may be made within the scope of the inventive concept.

I claim:

1. Audiometer apparatus having a tone generator (11) generating tone frequencies at predetermined frequencies or frequency ranges;
    a controlled amplifier (12) coupled to the tone generator (11),
    said controlled amplifier having an amplification level control input (21);
    a electroacoustic transducer (13) coupled to and receiving the output from the controlled amplifier (12) and providing an actual acoustic signal;
    an acoustic-electro transducer (31) acoustically coupled to the electroacoustic transducer (13), and an analog/digital converter (30) connected to and digitizing the output from the acoustic-electro transducer (31);
    means digitally storing data representative of frequencies and output levels of a test program;
    and means to calibrate the apparatus to ensure actual output by said electroacoustic transducer (13) in accordance with frequency and level data of the test program, comprising
    an electrically programmable read-only memory (EEPROM) (15) connected to and controlled by the test program storage means (22);
    a calibrating stage (17, 18) having controllable calibrating elements (181) and means controlled by the read-only memory (15) coupled to and controlling the respective calibrating elements in accordance with digital data signals from the test program storage means (22);
    wherein the calibrating elements comprise a plurality of resistors (181) forming a resistance chain connected between a source of voltage and a reference potential;
    the means controlling the calibrating elements includes switching means (171, 172, 173) selectively switching respective resistors (181) in the resistance chain under control of data signals derived from the memory (15);
    a fixed measuring resistor ($R_N$) serially connected to the resistance chain (181);
    means (185) coupled to said amplifier controlled input (21) for deriving a calibration correction voltage ($U_K$) across the measuring resistor ($R_N$);
    and wherein the test program storage means receives the output from the analog/digital converter (30) and includes means for comparing said actual acoustic output signal with the stored frequency and level data in the test program storage means to derive a deviation signal;
    and means for recording the deviation signal as a calibrating signal in the read-only memory (15).

2. The audiometer apparatus of claim 1, including controlled connection means (28, 34) connected to the test program storage means;
    and wherein the test program storage means stores test programs specific to a specific electroacoustic transducer (13),
    the controlled connection means being connected to the respective specific electroacoustic transducer (13).

3. The audiometer apparatus of claim 1, wherein the tone generator is operable in a plurality of modes including generation of specific frequencies and generation of frequency bands;
    and including a controlled connection means (28) connecting the test program storage means (22) and the tone generator to control the mode of tone generated by the tone generator in accordance with a test program stored in the test program storage means.

4. The audiometer apparatus of claim 3, wherein one of the modes of operation of the tone generator comprises generation of amplitude-modulated frequencies;
    and the controlled connection means controls operation of the tone generator at said selected mode.

5. The audiometer apparatus of claim 1, wherein the calibrating elements and the memory (15) are subdivided, respectively, in groups of coarse, intermediate and fine calibration elements, and memory sections, respectively.

6. The audiometer apparatus of claim 5, wherein the read-only memory (15) comprises an electronically erasable programmable and reprogrammable read-only memory (EEPROM).

7. The audiometer apparatus of claim 1 wherein said switching means (171, 172, 173) selectively short circuits respective resistors in the resistance chain.

8. The audiometer apparatus of claim 1 wherein the resistors (181) in the resistance chain and the memory (15) are subdivided, respectively, into respective calibrating stages for different degrees of resolution of calibration.

9. Audiometer apparatus having means to calibrate the apparatus, comprising
    means (22) for storing a test program;
    a non-volatile read-only memory (15) connected to and controlled by the test program storage means;
    a calibrating stage (17, 18) having controllable calibrating elements (181)
    wherein the calibrating elements comprise a plurality of resistors (181) forming a resistance chain connected between a source of voltage and a reference potential;
    the means controlling the calibrating elements includes switching means (171, 172, 173) selectively switching respective resistors (181) in the resistance chain under control of data signals derived from the memory (15);
    a fixed measuring resistor ($R_N$) serially connected to the resistance chain (181);
    means (185) for deriving a calibration correction voltage ($U_K$) across the measuring resistor ($R_N$);
    means (17) controlled by the non-volatile read-only memory (15) coupled to and controlling the respective calibrating elements (181) in accordance with control data signals from the test program storage means (22);

and wherein the memory (15) and the calibrating elements (181) are subdivided into respective calibrating stages for different degrees of resolution of calibration.

10. The audiometer apparatus of claim 9, wherein the memory comprises an electronically erasable programmable and reprogrammable read-only memory (EEPROM) (15).

11. The audiometer apparatus of claim 9, wherein the different degrees of resolution comprise coarse, intermediate and fine calibration.

12. The audiometer apparatus of claim 9 wherein said switching means (171, 172, 173) selectively short circuits respective resistors in the resistance chain.

* * * * *